US 6,678,549 B2

(12) United States Patent
Cusimano et al.

(10) Patent No.: US 6,678,549 B2
(45) Date of Patent: Jan. 13, 2004

(54) COMBINED PHYSIOLOGICAL MONITORING SYSTEM

(76) Inventors: MaryRose Cusimano, 7481 W. Oakland Park Blvd., Suite 305, Ft. Lauderdale, FL (US) 33319; Scott J. Zeff, 7481 W. Oakland Park Blvd., Suite 305, Ft. Lauderdale, FL (US) 33319

(*) Notice: Subject to any disclaimer, the term of this patent is extended or adjusted under 35 U.S.C. 154(b) by 244 days.

(21) Appl. No.: 10/002,942

(22) Filed: Nov. 15, 2001

(65) Prior Publication Data

US 2003/0135129 A1 Jul. 17, 2003

(51) Int. Cl.[7] .................................................. A61B 5/04
(52) U.S. Cl. ..................................................... 600/546
(58) Field of Search .......................... 600/546, 595, 600/587, 300; 601/24; 482/4, 114, 120, 127, 51

(56) References Cited

U.S. PATENT DOCUMENTS 5,513,651 A * 5/1996 Cusimano et al. .......... 600/595
5,885,231 A * 3/1999 Cramer et al. ............. 600/595
6,152,855 A * 11/2000 Dean et al. ..................... 482/4

* cited by examiner

Primary Examiner—Max F. Hindenburg
Assistant Examiner—Brian Szmal
(74) Attorney, Agent, or Firm—Albert O. Cota (57) ABSTRACT

A combined physiological monitoring system (CPMS) (10) which provides an electrodiagnostic functional assessment (EFA) to determine the relative age and severity of a myofasical injury. The EFA utilizes data serviced by electromyography (EMG) sensors which measures the amplitude and frequency of a muscle group; functional capacity evaluation (FCE) sensors, which measure the lift, pull and push capability; range-of-motion (ROM) sensors, which measure the range of motion in the cervical, thoracic, lubosacral, upper and lower extremities; and a grip and pinch sensor, which measures a person's grip and pinch strength. The CPMS (10), allows the measurement to be conducted individually or be integrated and conducted simultaneously in combination with EKG activity, blood flow and nerve conduction velocity. The CPMS (10) which can be designed to be portable, operates in combination with a software program (80) which resides in a dedicated laptop computer (82).

30 Claims, 5 Drawing Sheets

COMBINED PHYSIOLOGICAL MONITORING SYSTEM

TECHNICAL FIELD

This invention pertains to the general field of electro-diagnostic systems and more particularly to a system which monitors muscles in various ranges of motion such as lifting, pulling, pushing, gripping and pinching while simultaneously monitoring physiological functions such as temperature, heart rate and skin response.

BACKGROUND ART

Many physicians encounter patients with complaints that involve injuries of the soft tissues, particularly those soft tissues of the paraspinal muscles. In many cases objective findings are obvious, but a percentage of patients have injuries that, while subtle, still cause symptoms that bring them to the attention of a care provider or specialist. In other cases, the injuries many be less recent, which provide no apparent physical findings. Direct palpation of soft tissues can, in some cases, reveal the nature or type of injury, but this manner of diagnosis relies on static testing. For some subject, problems may only be encountered during activity. Quantifying these dynamic condition of the soft tissues is problematic.

Range of motion testing is often relied upon to determine the cause, yet measuring the muscle activity during range of Motion testing is difficult. The extent to which a patient exerts him or herself also presents a subjective bias. If muscle activity could be recorded during range of motion testing, the extent to which the muscles or muscle groups are activated and to what degree would provide helpful information about the nature of the soft tissue injury.

The Mayo Clinic confirmed in their studies on sagittal gait patterns and knee joint functions that static measurements do not correlate well with true functional assessment of movement. As part of their conclusions, they recommended the use of functional assessments as a routine diagnostic tool in a similar manner as an electrocardiogram (EKG). In this setting, the use of tests like magnetic resonance imaging (MRI) or X-rays are of little use, since they are static tests and not specifically designed to evaluate soft tissue damage and the subsequent change in function. Therefore, there is a growing need within the medical, insurance and industrial communities for an objective analysis of biomechanics on a functional level.

Myofacial injuries represent a significant medical problem, with back pain accounting for a large number of medical visits. Carpal tunnel syndrome (CTS) and repetitive stress injuries (RSI) account for the most days lost and is currently one of the most costly health problems. The cost of this health problem is expected to increase because OSHA has passed a musculoskeletal disorder standard for repetitive stress injuries. With the implementation of the American's with disability (ADA) law, worker's compensation claims such as (CTS) can now sue in the federal court system, allowing for suits in excess of 10 million dollars. These expensive claims could damage the economy and force employers to go outside of the United States.

A recent study revealed that over 45 percent of individuals who have undergone CTS release surgery mere no better two years past the surgical intervention because they were misdiagnosed. The individuals probably had cervical pathology that can refer pain and mimic the symptoms of CTS, ulnar neuopathy, cubital tunnel, tendonititis, DeQuarian's syndrome i.e., repetitive stress injuries. The problem is that until the development of the instant invention, there was no way to ascertain if the problem was proximal, cervical or distal.

In the past, many doctors have prescribed a profalatic work restriction limiting the amount an individual can lift. More often than not, the lifting restriction is too general and too limiting which prohibits the individual from returning back to their visual or any job. For example, a typical work restriction of not lifting over 50 pounds is highly restrictive. Doctors impose this restriction because they have no means of evaluating the muscle and disc pathology during movement.

The inventive combined physiological monitoring system (CPMS) solves many of the above problems on data gathering by combining up to 32 channels of proprietary surface EMG, up to 12 range of motion channels, two CPMS sensors and a grip strength. There is also room for at least two cables of electromyography (EMG). The CPMS also combines two channels of nerve conduction velocity (NCV) to apply a current to monitor NCV with temperature control and pre-set electrodes. The CPMS can also be designed to operate with utility power or to be battery operated to allow an individual to be monitored anywhere, including the worksite.

A search of the prior art did not disclose any patents that read directly on the claims of the instant invention. However, the following U.S. patents were considered related:

| U.S. Pat. No. | INVENTOR | ISSUED |
| --- | --- | --- |
| 5,513,651 | Cusimano, et al | 7 May 1996 |
| 5,462,065 | Cusimano, et al | 31 Oct. 1995 |
| 5,042,505 | Mayer, et al | 27 Aug. 1991 |
| 4,688,581 | Moss | 25 Aug. 1987 |
| 4,667,513 | Konno | 26 May 1987 |

The U.S. Pat. Nos. 5,513,651 and 5,462,065 disclose an integrated movement analyzing system that utilizes surface electromyography in combination with range of motion and functional capacity testing to monitor muscle groups in the human body. The system consists of an integrated movement analyzer (IMA) that receives inputs from surface EMG electrodes, a range of motion arm (ROMA), and a functional capacity sensor. When performing Upper and lower back testing, the ROMA is connected between the patient's upper back and lower back by a shoulder harness and a waist belt. For cervical testing, the ROMA is connected between the patient's head and upper back by a cervical cap and the shoulder harness. The output of the IMA is provided via an analog to digital converter to a computer. The computer in combination with a software program produces an output consisting of comparative analytical data.

The U.S. Pat. No. 5,042,505 discloses an electronic device for measuring relative angular positional displacement and annular range of motion for body segments and articulating joints of the human skeleton. The device has a hand-held interface unit which is placed against the body segment or joint to be tested. Mounted within the housings of the interface unit is a shaft with a pendulum at one end and an optical encoder at the other. As the body segment rotates or the joint articulates, the pendulum swings in the direction of gravity, causing the shaft to rotate. The optical encoder generates an electrical signal representative of the amount of rotation of the shaft. The generated signal is fed to a microprocessor which processes the information and can produce on a display the change in angular position relative to initial angular position or the angular range of motion of the body segment or articulating joint.

The U.S. Pat. No. 4,688,581 discloses an apparatus and a method for non-invasive in vivo determination of muscle fiber composition. The method includes the steps of electrically stimulating a chosen muscle; determining the stimulation current; measuring the electrical potential of the muscle; the contraction timer and the force produced by the contraction; and by intercorrelating the data by multiple regression, determining the type, percentage and size of muscle fibers within the muscle stimulated. Apparatus for determining the muscle composition includes a muscle stimulator of controlled voltage electromyogram equipment, and a force transducer providing a tension curve as well as force measurements.

The U.S. Pat. No. 4,667,513 discloses an apparatus and a method for estimating the degree of the fatigue and pain of muscles. The apparatus composes subjects of different weights on the same basis by deriving the variation in the muscular strength such as dorsal muscular strength, shoulder muscular strength, grasping power and the like. An analogous electric signal integrates the muscular output on one hand, and provides an integrated value of the electromyogrammatic amplitude by processing the voltage induced from the muscle to be tested through an electromyogram amplitude and a waveform processor. The ratio between these integrated values, after correcting the ratio with a weight/muscular strength coefficient is digitally displayed.

For background purposes and as indicative of the art to which the invention relates, reference may be made to the following remaining patents found in the search:

| U.S. Pat. No. | INVENTOR | ISSUED |
| --- | --- | --- |
| 5,056,530 | Butler, et al | 15 Oct. 1991 |
| 5,050,618 | Larsen | 24 Sep. 1991 |
| 5,042,505 | Meyer, et al | 27 Aug. 1991 |
| 5,038,795 | Roush, et al | 13 Aug. 1991 |
| 5,012,820 | Meyer | 7 May 1991 |
| 4,938,476 | Brunell, et al | 3 Jul. 1990 |
| 4,928,709 | Allison, et al | 29 May 1990 |
| 4,886,073 | Dillion, et al | 12 Dec. 1989 |
| 4,845,987 | Kenneth | 11 Jul. 1989 |
| 4,834,057 | McLeod, Jr. | 30 May 1989 |
| 4,805,636 | Barry, et al | 21 Feb. 1989 |
| 4,800,897 | Nilsson | 31 Jan. 1989 |
| 4,742,832 | Kauffmann, et al | 10 May 1988 |
| 4,667,513 | Konno | 26 May 1987 |
| 4,586,515 | Berger | 6 May 1986 |

DISCLOSURE OF THE INVENTION

The combined physiological monitoring system (CPMS) consist of a portable, non-loading electronic unit that simultaneously monitors muscle activity with standard electrode. The muscle groups in the human body, including cervical, midback, low back and upper and lower extremities, are monitored. The CPMS also uses the gold standard in combination with a load cell and strain gauge to determine a person's lifting, gripping and range-of-motion capability. The CPMS functions with a dedicated computer and a proprietary software program, entitled Patient Data Acquisition System (PDAS) which correlates muscle activity with a force produced by a person. The design of the CPMS allows electromyography (EMG), range-of-motion, grip assessment and functional assessment to be conducted during a single testing session.

During an injury to a muscle and/or fascial elements, many pathophysiological processes occur which follow a predictable pattern. When a muscle is strained, the fibers of that muscle are damaged and cells within the muscle are ruptured. These ruptured cells release substances which cause the muscle to reflexively tighten. Muscles that cause an action (agonist) and muscles which prevent the action (antagonist) are monitored. Muscle groups which are distant from the injury site may not be performing their proper function since they are compensating for the loss of function due to the injury. The greater the pattern of compensation the more longstanding is the injury.

The EMG provided by the CPMS will record a signal of increased amplitude and frequency from a muscle which is characteristic of an acute injury. The process of aging an injury is multi-factorial and involves not only muscle groups, but their interrelationship with each other. An electrodiagnostic functional assessment (EFA) provided by the CPMS can monitor up to a total of 19 muscle groups simultaneously.

By understanding the natural progression of a myofascial injury, and the information provided by the CPMS, the relative age of an injury can be determined.

Figure 1:
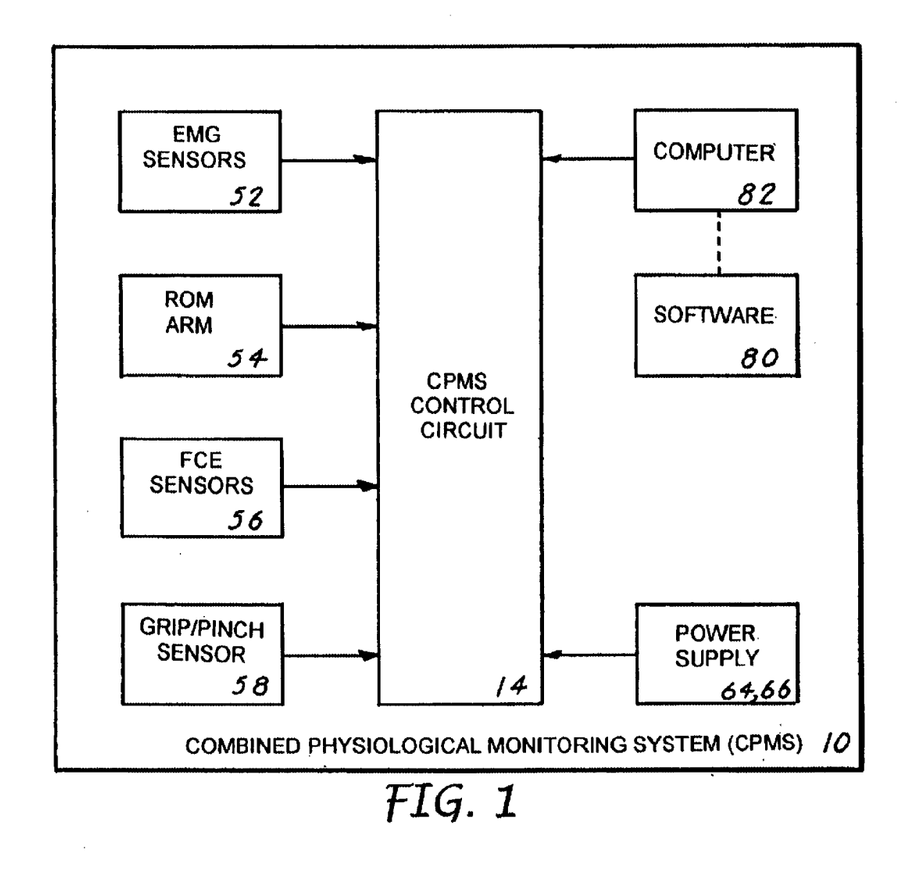
FIG. 1 is a block diagram showing the basic elements that comprise the combined physiological monitoring system (CPMS).

In its most basic form, the CPMS is comprised of the following elements, which are shown in FIG. 1 and described in the Best Mode for Carrying out the invention:

a) a plurality of EMG sensors, b) a range-of-motion (ROM) arm, c) a plurality of functional capacity evaluation (FCE) sensors,    d) a grip sensor,    e) a pinch sensor,    f) a power supply    g) a computer,    h) software, and    i) a CPMS control circuit.

In view of the above disclosure, the primary object of the CPMS is to monitor selective muscle activity in a human body, which includes cervical, thoracic, upper and lower extremities and lumbosacral. The CPMS can simultaneously correlate the muscle activity with EMG, range-of-motion, grip assessment and a functional assessment.

In addition to the primary object of the invention, it is also an object of the invention to produce a CPMS that:

identifies malingering persons, workers who may be magnifying symptoms, and most importantly, in diagnosing real injuries and allows the acquired data to be reviewed to determine appropriate treatment,    assesses the actual extent of myofascial injuries that might be job or accident related,    allows muscle pathology to be assessed above and below the area of the reported injury which then allows the total extent of an injury to be established to determine future treatment, the probability of permanent disability and the need for potential vocational rehabilitation,    provides a real time diagnosis of muscle activity,    provides a powerful tool for establishing an evaluation and treatment program,    can assess chronic versus acute injuries by evaluating muscle compensation,    can assist physicians who care for professional or high level college athletes, in determining the extend of sports-related musculoskeletal injuries, and provide accurate data that can be used in designing site-specific treatment protocols, thus allowing a more rapid, predicable and safe return to competition. It can also be used in pre-participation physical examinations and allow trainers to address otherwise undiagnosed deficiencies, and can assess the clinical significance of disc pathology.

In summary, the CPMS identifies the severity of injuries allows future diagnostic and treatment programs to be established that take into account both the needs of the injured person and the need to contain the runaway costs of potential long term or unsubstantiated cases.

These and other objects and advantages of the present invention will become apparent from the subsequent detailed description of the preferred embodiment and the appended claims taken in conjunction with the accompanying drawings.

BEST MODE FOR CARRYING OUT THE INVENTION

The best mode for carrying out the invention is presented in terms of a preferred embodiment for a combined physiological monitoring system (CPMS) 10. The CPMS Performs an electrodiagnostic functional assessment (EFA) by analyzing muscle activity by means of electromyography (EM). When using EMG, a standard silver—silver chloride electrode is attached to a muscle or muscle group. The electrical activity of the muscle or muscle group is measured and recorded.

The muscle groups monitored by the CPMS 10 are: cervical, thoraic, upper extremity, lower extremity and lumbosacral. Data pertaining to each muscle group is typically taken in the following five steps, while the monitored muscle or muscle group is:

1) at rest,
2) going through a range of motion protocol,
3) at rest
4) being applied a gripping, lifting and/or pulling force, and
5) at rest.

The above test allow the CPMS 10 to determine muscle tone (contracture amplitude) muscle spasms (frequency) blood flow to muscles (vasoconstrive states), muscle activity (frequency and recruitment patterns), and muscle responses (fatigue). Thus, the CPMS can assess the condition and the dynamic functions of any particular muscle or muscle group.

In a typical configuration, the CPMS 10 is comprised of:

a) up to 30 channels of surface electromyography (EMS), wherein each channel can be designed to incorporate an analog-to-digital converter (ADC), b) two channels of nerve conductive velocity (NCV) with temperature control and pre-set electrodes, c) two channels for receiving range-of-motion (ROM) arms, d) two channels for receiving functional capacity evaluation (FEE) sensors, e) a channel for receiving a grip strength sensor, and f) a channel for receiving a pinch strength sensor.

The electrodiagnostic functional assessment (EFA) can be conducted one test at a time or can be combined with EMG, ROM, FCE and the grip and pinch strengths to provide an integrated test, which is conducted during a single test session. The CPMS 10 can also be configured to function as an electrocardiagram (EKG) and to allow additional physiological functions to be added such as temperature, heart rate and skin response. To function as an EKG, the CPMS is modified by using only eight channel(s). The EKG Provided by the CPMS is better because there is no movement artifact and can simultaneously monitor blood flow.

The preferred embodiment of the CPMS 10, as shown in FIGS. 2–7, is comprised of the following major elements: a CPMS control circuit 14, a leads-off circuit 50, an EMG sensor 52, a range of motion (ROM) arm 54, functional capacity evaluation (FCE) sensors 56, a grip and a pinch sensor 58, a power supply interface circuit 62, an analog power supply 64, a digital power supply 66, an EMG cable assembly 70, a patient data acquisition system (PDAS) software program 80 which resides in a PC computer 62, and a computer/system interface circuit 84.

The CPMS control circuit 14 has means for processing the digital and analog signals which operate the CPMS 10. The circuit 14, which is shown in its overall relationship with the CPMS 10 in FIG. 2 and in detail in FIG. 3, is partitioned into an analog section 16, a digital section 40 and a power distribution circuit 48. The analog section 16 is comprised of an electromyography (EMG) leads connection circuit 18, an EMG front end circuit 20, a leads-off detection circuit 22, a leads-off display circuit 24, a range of motion (ROM)/functional capacity evaluation (FCE)/grip and pinch interface circuit 26, a ROM front end circuit 28, an FCE/grip and pinch front end circuit 30, and a data acquisition circuit 34.

The EMG leads connection circuit 18 has means for determining the structural integrity of the leads from the EMG sensors 52, and can accommodate from one to nineteen leads. The circuit 18 is connected to a first signal, a second signal and a third signal. The first signal is connected to the EMG sensor 52 and the second signal is connected to the EMG front end circuit 20 which has means for assessing the muscle activity sensed by the EMG sensors 52. The circuit 20 produces a fourth signal that is applied to the data acquisition circuit 34 for further processing.

The third signal from the circuit 18 is connected to the leads-off detection circuit 22, which has means for determining if the EMG sensor leads are properly attached by measuring the impedance of the muscle and the surrounding skin area. The circuit 22 is also connected to a fifth, sixth and seventh signal. The fifth signal is applied to the data acquisition circuit 34 for further processing, the seventh signal is connected to the EMG sensors 52 and the sixth signal is applied to the leads-off display circuit 24 which has means for producing a display when an electrode attached to a muscle or the surrounding skin area is not properly attached. This determination is made by measuring the impedance of each electrode. If the impedance is not at a correct level, a corresponding LED illuminates. The circuit 24 allows up to 32 electrodes to be utilized, wherein each electrode pertains to a specific muscle placement. The circuit 24, which functions in combination with the circuit 22, is connected to the circuit 22 Via the sixth signal.

The range of motion (ROM)/functional capacity evaluation FCE/grip and pinch interface circuit 26 is shown as a single element for purposes of explanation. The circuit 26 is connected to an eighth, ninth and tenth signal which are connected respectively to a ROM sensor 54, a plurality of FCE sensors 56 and a grip and pinch sensor 58, which are further described infra. The circuit 26 also produces an eleventh signal which is applied to the ROM front end circuit 28 and a twelfth signal applied to the FCE/grip and pinch front end circuit 30. The ROM front end circuit 28 has means for receiving and processing the data applied from the circuit 26 via the eleventh signal. The received data is amplified and filtered prior to producing a thirteenth digital signal that is applied to the data acquisition circuit 34 for further processing.

The FCE/grip and pinch front end circuit 30 has means for receiving and processing the data applied from the circuit 26 Via the twelfth signal. The received data is amplified and filtered prior to producing a fourteenth digital signal that is applied to the data acquisition circuit 34 for further processing.

The data acquisition circuit 34 is designed to include a first DAQ module 34A and a second DAQ module 34B. The DAQ modules function in combination to receive the fourth signal from the circuit 20, the fifth signal from the circuit 22, the thirteenth signal from the circuit 28 and the fourteenth signal from the circuit 30. The input signals are processed by the circuit 34 to produce a fifteenth digital signal that is applied to the digital section 40 for further processing as shown in FIG. 3.

The digital section 40 of the CPMS control circuit 14 is comprised of an optical isolation circuit 42, a date processing circuit 44 and a computer interface circuit 46.

The optical isolation circuit 42 has means for isolating a person from external electrical power sources which may harm a person and can cause erroneous test readings. The circuit 42 is connected to the data acquisition circuit 34 via the fifteenth signal, to the data processing circuit 44 via a seventeenth signal, and to the computer interface circuit 46 via an eighteenth signal. The circuit 42 also has connected a sixteenth digital power signal. The data processing circuit 44, which is designed to process, transfer and store data, is also connected to the computer interface circuit 46 via a nineteenth signal.

Figure 2:
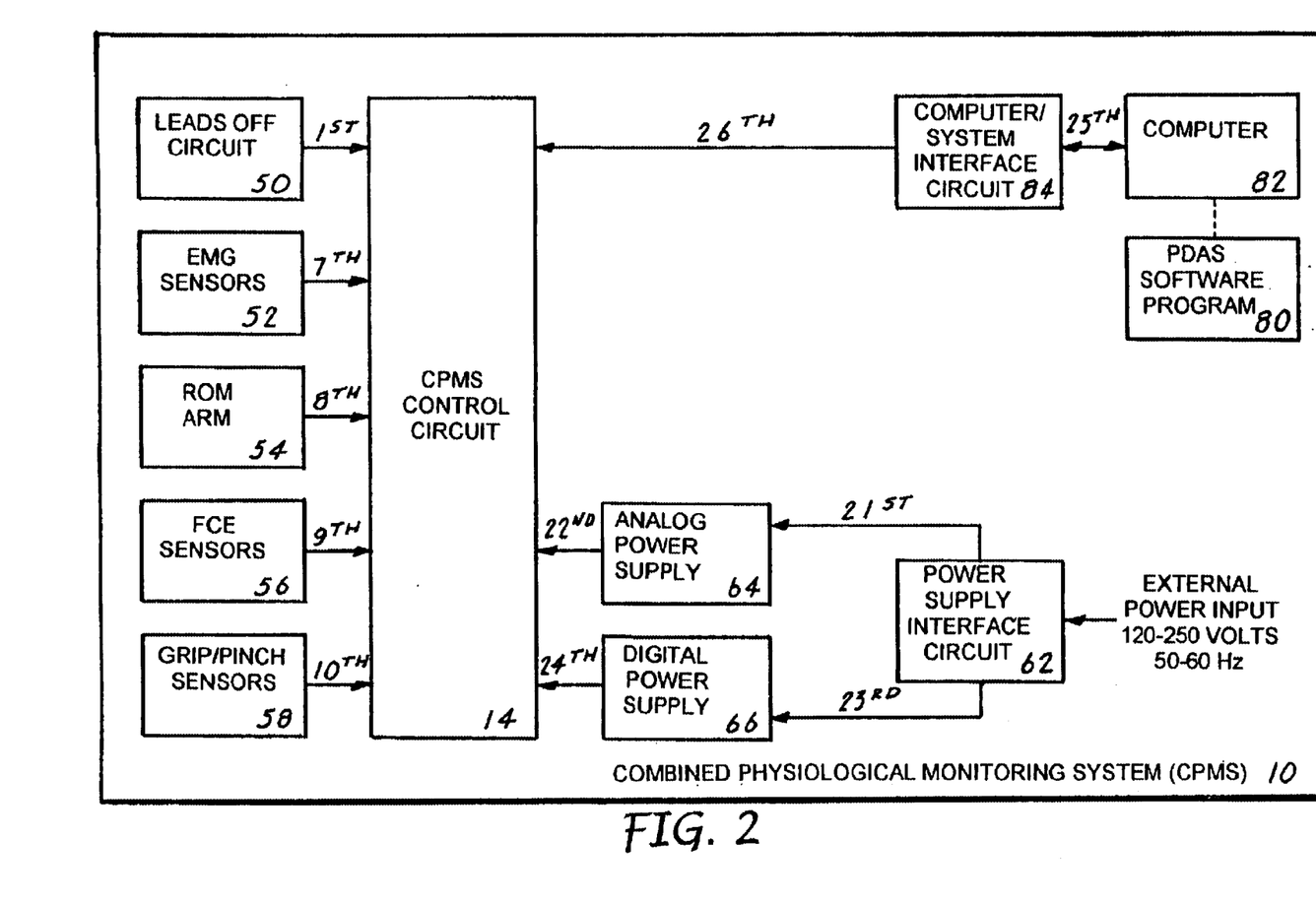
FIG. 2 is a detailed block diagram of the overall combined physiological monitoring system (CPMS).
Figure 3:
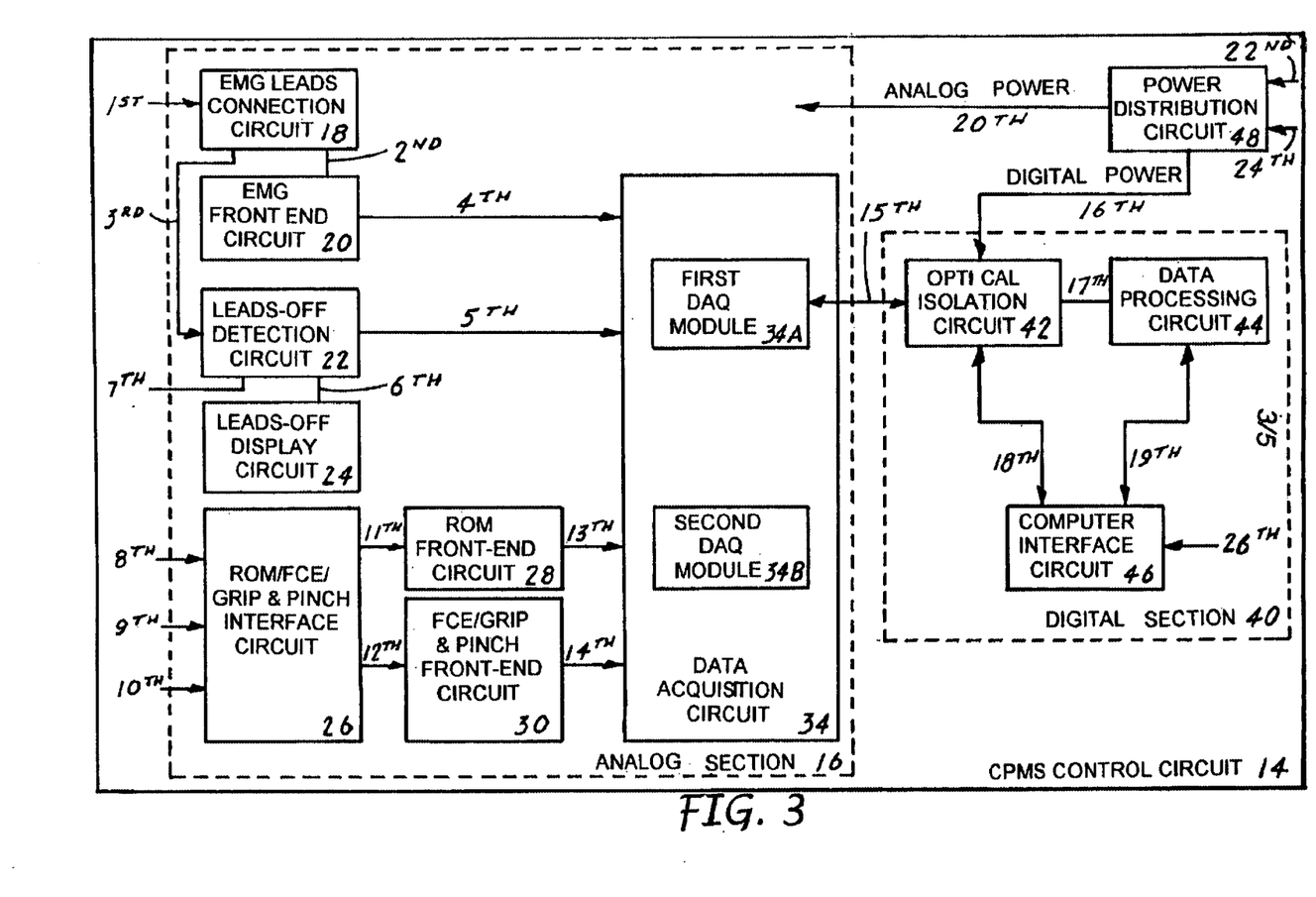
FIG. 3 is a detailed block diagram of the CPMS control circuit which is integral element of the CPMS.

The computer interface circuit 46 is also connected to a twenty-sixth signal, as shown in FIGS. 2 and 3, that is applied from the computer/system interface circuit 84 which interfaces with the computer 82 via a twenty-fifth signal. The circuit 46 can be designed to operate with a Universal Serial BUS (USB), a Firewire (IEEE 1394) bus or a parallel port. The circuit 46 is designed to interface with the software 80 via the computer 82.

The final element of the CPMS control circuit 14 is the power distribution circuit 48, which is applied a twenty second analog power signal and a twenty-fourth digital power signal as shown in FIG. 2. The circuit 48 has means for regulating and distributing digital power to the digital circuits in the CPMS control circuit 14 via the optical isolation circuit 42, which is applied the sixteenth signal from the circuit 48. The circuit 48 also applies analog power to the analog section 16 of the CPMS control circuit 14 via a twentieth signal.

The preferred embodiment of the overall combined physiological monitoring system (CPMS) 10 is shown in FIG. 2, which includes the signal inputs applied to the CPMS control circuit 14 as described above. The first signal applied to the circuit 14 is from the leads-off circuit 50, which includes a means for determining if an electrode is not properly attached to a muscle. The first signal is sent sequentially to the circuit 18 and 22, and to the leads-off display circuit 24 where an improperly-attached lead is displayed and a signal is sent to the software 80 to shut off the CPMS 10. The EMG sensors 52 produce the seventh signal which is applied to the leads-off detection circuit 22 in the CPMS circuit 14. The EMS sensors 52 sense the amplitude and frequency of various muscles or muscle groups. This data is used to monitor muscle, EKG or blood flow activity.

The range of motion (ROM) arm 54 includes a means for measuring the range of motion in the cervical, thoracic, lumbosacral, upper extremity, lower extremity and digits. The RON arm 54 measures a person's lateral movement, flexion, extension and rotation, each having six degrees of freedom. The ROM arm 54 incorporates two triaxial, silicon, micromatched accelerometer systems, wherein each system includes three hermetically-sealed ADXL05 accelerometers. The device 54 has a bandwidth of 1 kHz to 4 kHz and, if required, can be a-c coupled. Optimally, the ROM arm 54 can be designed with precision potentiometers having three joints for monitoring segmental changes plus range of motion. All the analog data collected is converted to a d-c signal that is applied via an eighth signal to the ROM interface circuit 26 located in the CPMS control circuit 14.

The functional capacity evaluation (FCE) sensors 56 include a means for measuring a person's lift, pull and push capability. The FCE sensor function by utilizing load cells which convert an analog signal produced by the sensors to a corresponding digital signal that is applied via a ninth signal to the FCE interface circuit 26 located in the CPMS control circuit 14.

The grip/pinch sensors 58 include a means for measuring a person's hand grip strength and pinch strength. The hand grip strength is measured by a load sensor that produces an analog signal proportional to the grip force. The analog grip force signal is converted by an ADO to a corresponding digital signal that is applied via a tenth signal to a grip interface circuit 26 located in the CPMS control circuit 14. The pinch strength is comprised of a load button-load cell. The load button-load cell, which has a range of 0 to 50 lbs, is placed between the thumb and index finger and squeezed to produce an analog signal which is likewise converted to a digital signal that is applied, via the tenth signal, a pinch interface circuit 26, also located in the CPMS control circuit 14.

The power input to the CPMS 10 is provided by an external power source that is applied to a power supply interface circuit 62. The circuit 62 has means for receiving and processing a power input ranging from 120–250 volts at a frequency of 50 or 60 Hz. The circuit 62, which incorporates circuit protection in the form of a circuit breaker or fuse, produces a twenty-first analog power signal and a twenty-third digital power signal.

The analog powers supply 64, which is connected to the twenty-first signal, produces a twenty-second output signal consisting of a regulated 5-volts d-c which powers the analog circuits in the CPMS control circuit 14. Likewise, the digital power supply 66, which is isolated from the analog power supply 64, is connected to the twenty-third signal and produces a twenty-fourth output signal consisting of a regulated 5-volt d-c which powers the CPMS 10.

Figure 4:
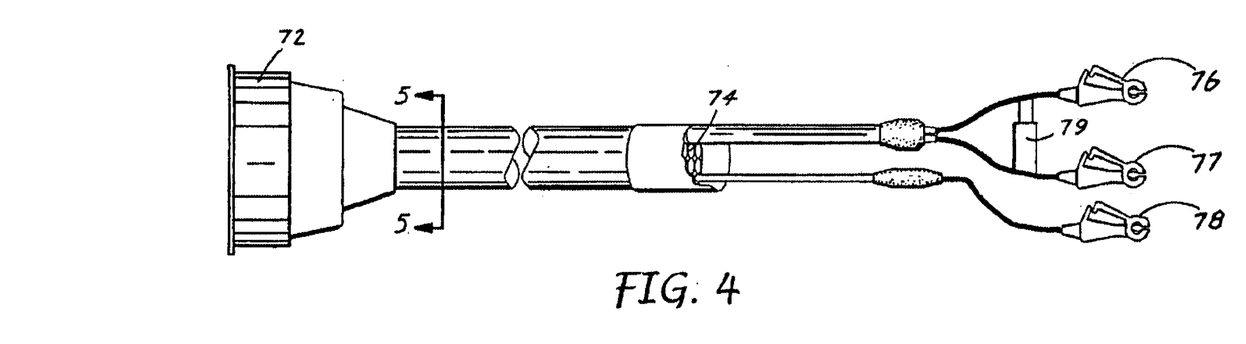
FIG. 4 is a side elevational view of an electromyography (EMG) cable assembly.
Figure 5:
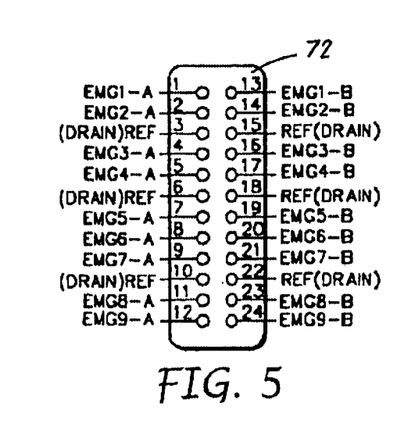
FIG. 5 is an elevational view of the multi-pin connector of the EMG cable assembly.
Figure 6:
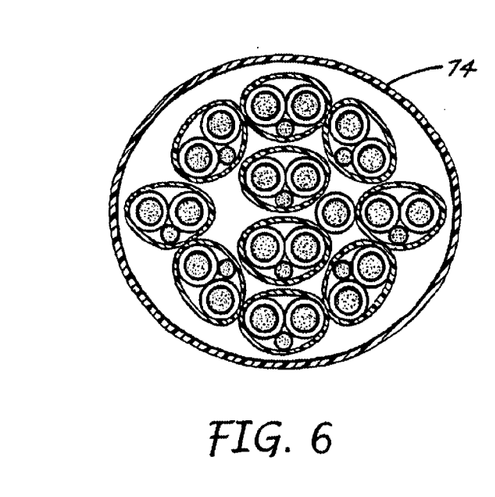
FIG. 6 is a sectional view of the EMG cable assembly taken along the lines 5—5 of FIG. 3.

The EMG cable assembly 70, as shown in FIGS. 4, 5 and 6, is designed to connect the EMG sensors to the muscle or muscle group of a person being tested. The cable 70 includes a multi-pin connector 72, as shown in FIGS. 4 and 5, ten shielded wire pairs 74, as shown in FIG. 6, and three EMG electrodes 76, 77 and 78, as shown in FIG. 4. The first electrode 76 is active and is common with the second electrode 77 which is also active. The third electrode 78 attaches to circuit ground.

The EMG cable assembly 70 incorporates a separation bar 79, as shown in FIG. 4, which can be locked at a distance between 3 to 5 inches. The separation bar 79 allows the two active electrodes 76, 77 to remain isolated from each other. Additionally, the EMG cable assembly 70 can be designed to include a temperature sensor (not shown) which allows temperature readings to be taken in combination with other EMG sensor readings.

Figure 7:
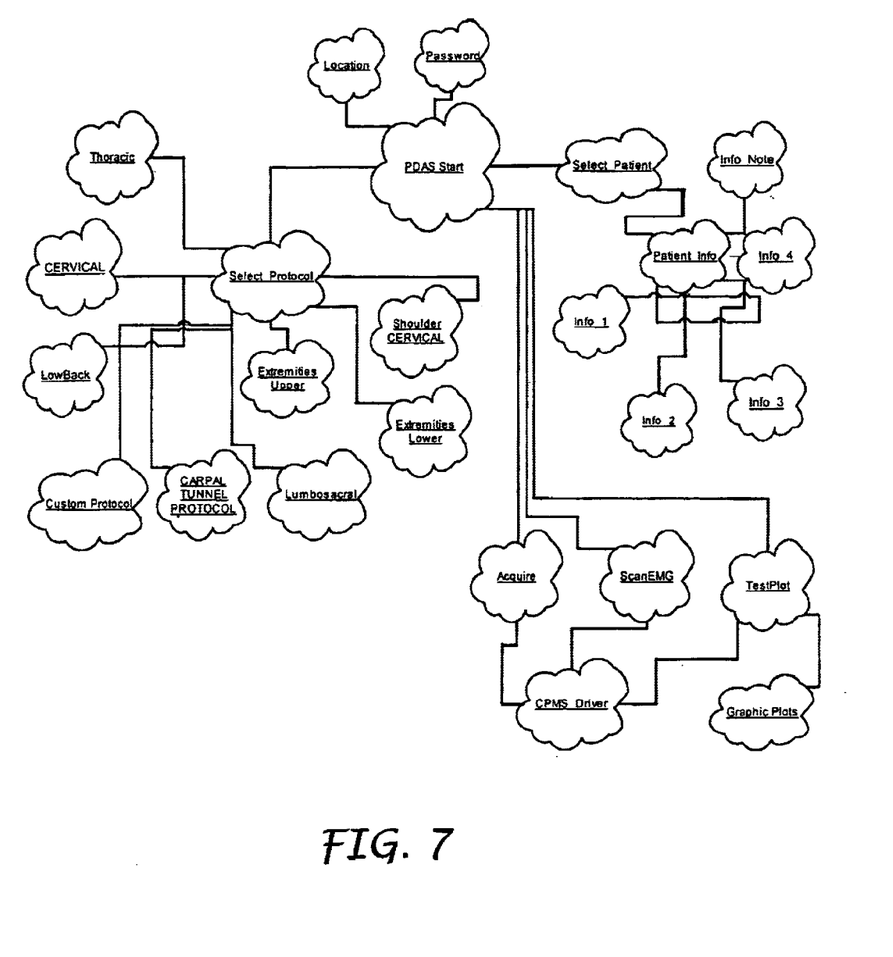
FIG. 7 is a module flow diagram of the CPMS spatent Data Acquisition System (PDAS) software program.

The Patient Data Acquisition system (PDAS) software program 90, as shown in FIG. 7, is designed to provide control and data collection for the combined Physiological monitoring System (CPMS) 10. The software 80 provides error detection, interactive computer interface and resides in a dedicated PC computer 82, which preferably consists of a laptop computer 82 which operates at least 400 MHz and has 64 to 256 megabytes of RAM. Additionally, the computer 82 incorporates at least a 10-gigabyte hard drive, a 14-inch active matrix LCD, an enhanced parallel port (EPP), a Universal Serial Bus (USB), a V.90 modem and 10baseT network cards. The operating system preferably consists of Ms windows or Linux, and the overall design methodology is Booch's object oriented design (OOD).

Thee computer 82 is connected via a twenty-fifth signal to a computer/system interface circuit 84 which allots the computer 82 to communicate with the CPMS 10 via the CPMS control circuit 14 as shown in FIG. 1.

The software 80 is comprised of nine major modules:
a) PDAS Start—provides start up routines and initialization routines for the CPMS 10. Upon startup a main window is displayed and user commands are concurrently sent to selected elements of the CPMS 10.
b) Location—provides routiness to verify the location of the selected CPMS element,
c) Password—provides access control over specialized routiness for demonstration purpose,
d) Select Patient—provides services to add a new patient, selects a previous patient for retest and selects a patient for demonstration, This module also calls Patient Info (described below) to collect patent information.
e) Patient Info—provides interactive forms for the collection of patient information. Five patient information forms are available: Info 1, Info 2, Info 3, Info 4 and Info-note. After all data is validated, control is returned to the Select Patient module which then returns control to the PDAS 74 Start module.
f) Select Protocol—provides control and message passing for eight specialized protocols and one custom protocol. Each protocol provides instructions to the patient and instructions on the placement of the EMG sensors. This module also provides support for the muscle groups: Cervical, thoracic, Upper Extremity, Lower Extremity, Lumbosacral, and chest.
g) Acquire—provide data captures routines based on messages from the Select Protocol module via the PDAS Start module. Data is collected and monitored via the CPMS. If a lead fail is detected during the data capture, the Acquire module cancels the data capture and sends a warnings to the SelectProtocol module via the PDAS Start module. A successful data capture results in a data file being saved to a disk.
h) ScanEMG—provides testing of the EMG channels. This module provides services to select a single channel or to select all channels for verification.
i) TestPlot—provides a strip chart for testing all channels and their functions.

Operation

To conduct an electrodiagnostic functional assessment (EFA) a Person's muscle activity is analyzed. This analyses is performed by attaching a set of electrodes from the CPMS to selected muscle groups and measuring their electrical activity. The muscle groups and the measurement process is as follows:

a) measure the cervical muscle group by placing a range of motion (ROM) arm on the top of a Person's head, take measurements while the person is:
(1) at rest,
(2) performing selected range of motion protocols, and
(3) at rest,
b) measure the thoracic muscle group by placing the ROM arm at the center of the person's mid back and on the shoulders, take measurements while the person is:
(1) at rest,
(2) performing selected range of motion protocols, and
(3) at rest,
c) measure the lumbosacral muscle group by, placing the ROM arm at the center of the person's low back, take measurements while the person is:
(1) at rest,
(2) performing selected range of motion Protocols and
(3) at rest,
d) measure the lower extremities muscle group by placing bilateral sets of electrodes on the front and back of a person's thigh and ankles; place the ROM arm on each leg at the hip and knee joint, take measurements while the person is:
(1) at rest,
(2) performing selected range of motion protocols, and
(3) at rest,
(4) performing selected range of motion protocols,
(5) at rest,
e) measures the foot muscle group by placing the ROM arm on the persons ankle, take measurements while the person is:
(1) at rest,
(2) performing selected range of motion protocols, and
(3) at rest
f) measure the upper extremities muscle group by placing the ROM arm on the person's head, on one shoulder and on one persons take measurements while the person is:
(1) at rest,
(2) performing selected range of motion protocols, and
(3) at rest,
(4) performing a grip test utilizing a grip sensor,
(5) at rest,
(6) performing a pinch test utilizing a pinch sensor which is Placed between the thumb and forefinger,
(7) at rests
g) measure the hand muscle group by placing the ROM arm on the person's wrist, take measurements while the person is:
(1) at rest,
(2) performing selected range of motion protocols,
(3) at rest, (4) performing a pinch test utilizing a pinch sensor which is placed between the thumb and the forefinger,
(5) at rest, and
h) measure the face muscle group by placing the ROM arm on top of TMJ, take measurements while the person is:
(1) at rest,
(2) Performing selected range of motion protocol, and
(3) at rest The muscle groups are classified as follows:
a) the cervical muscle group comprises: sternocleidomastoid, scalene, paracervical, and upper trapzii,
b) the thoracic muscle group comprises: mid trapezii, lower trapezii, paraspinal muscles T5–T8, T8–T12, terses, and seratus
c) the lumbosacral muscle group comprises: paraspinal muscles L1–L3, L5–L51, quaratus lumborum, gluteal muscles, abdominal, and hamstrings,
d) the lower extremities muscle group comprises: all muscles in pelvis, legs and feet,
e) the foot muscle group comprises: all muscles in feet,
f) the upper extremities muscle group comprises: bilateral SCUM, scalene, deltoid, biceps, triceps and wrist flexors/extensors,
i) the hand muscle group comprises: all muscles in the hands
h) the face muscle group comprises: fontalis, massater TMJ While the invention has been described in complete detail and pictorially shown in the accompanying drawings it is not to be limited to such details, since many changes and modifications may be made to the invention without departing from the spirit and the scope there of. Hence, it is described to cover any and all modifications and forms which may come within the language and scope of the claims.

What is claimed is:

1. A combined physiological monitoring system (CPMS) comprising:
a) a CPMS control circuit (CCC) having means for processing a set of signals which operate said CPMS,
b) a plurality of electromyography (EMG) sensors having means for sensing the amplitude and frequency of a person's muscle groups, wherein the output from said EMG sensors are applied to and processed by said CCC,
c) a range-of-motion (ROM) arm having means for measuring the person's range of motion, lateral movement, flexion, extension and rotation, wherein the output from said ROM arm is applied to and processed by said CCC,
d) a plurality of functional capacity evaluation (FCE) sensors having means for measuring the person's lift, pull and push capability, wherein the output of said FCE sensors are applied to and processed by said CCC,
e) a grip sensor having means for measuring the person's grip strength, wherein the output of said grip sensor is applied to and processed by said CCC,
f) a pinch sensor having means for measuring the person's pinch strength, wherein the output of said pinch sensor is applied to and processed by said CCC,
g) a power supply having means for converting an input of 120–250 volts at a frequency between 50–60 HZ to a regulated d-c voltage which powers said CPMS, and
h) a computer which operates in combination with software to provide control and data collection for the CPMS.

2. A combined physiological monitoring system (CPMS) comprising:
a) CPMS control circuit having means for processing a set of signals which operate said CPMS, wherein said circuit is partitioned into:
(1) an analog section comprising:
(a) an electromyography (EMG) leads connection circuit having means for determining the structural integrity of the EMG leads, wherein said circuit is connected to a first signal, a second signal and a third signal,
(b) an EMG front end circuit having means for assessing EMG muscle activity, wherein said circuit is connected to the second signal, and to a fourth signal,
(c) a leads-off detection circuit having means for determining if the EMG leads are properly attached, wherein said circuit is connected to said EMG leads connection circuit via the third signal and to a fifth, sixth and seventh signal,
(d) a leads-off display circuit having means for producing a display when an electrode attached to a muscle or a surrounding skin area is not properly attached, wherein said circuit is connected to said leads off detection circuit via the sixth signal,
(e) range-of-motion (ROM)/functional capacity evaluation (FCE)/grip and pinch interface circuit having means for processing signals derived from a person's range-of-motion, FCE, grip and pinch, wherein said circuit is connected to an eighth, ninth, tenth, eleventh and twelfth signal,
(f) a ROM front end circuit having means for further processing the signals applied from the ROM/FCE/grip and pinch interface circuit via the eleventh signal, wherein the applied signals are amplified and filtered prior to producing a corresponding digital thirteenth signal,
(g) an FCE/grip and pinch front end circuit having means for receiving and processing the signals applied from the ROM/FCE/grip and pinch interface circuit via the twelfth signal, wherein the data are amplified and filtered prior to producing a fourteenth output signal,
(h) a data acquisition circuit which includes a first DAQ module and a second DAQ module, wherein said circuit is applied the fourth signal from the EMG front end circuit, the fifth signal from the leads off detection circuit, the thirteenth signal from the ROM front end circuit and the fourteenth signal from the FCE/grip and pinch front end circuit, wherein the signals are processed by the data acquisition circuit in combination with the first and second DAQ modules to produce a fifteenth digital signal,
(2) a digital section comprising:
(a) an optical isolation circuit having means for isolating a patient from external electrical power sources, wherein said circuit is connected to said data acquisition circuit via the fifteenth signal, wherein said circuit is also connected to a sixteenth digital power signal, a seventeenth signal, and an eighteenth signal,
(b) a data processing circuit designed to process, transfer and store data wherein said circuit is connected to said optical isolation circuit via the seventeenth signal, wherein said circuit is also connected to a nineteenth signal,
  (c) a computer interface circuit which is designed to interface with said CPMS, wherein said circuit is connected to the optical isolation circuit via the eighteenth signal and to said data processing circuit via the nineteenth signal, wherein said circuit is also connected to a twenty-seventh signal,
b) a power distribution circuit that is applied a twenty second analog power signal and a twenty fourth digital power signal, wherein said circuit having means for regulating and distributing digital power to the digital circuits in said CPMS control circuit via said optical isolation circuit which is applied the sixteenth signal from said power distribution circuit, and analog power to said analog section of said CPMS control circuit via a twentieth signal,
c) a leads-off circuit having means for determining if an electrode is improperly attached to a muscle, wherein said circuit is connected to said CPMS control circuit via the first signal,
d) a set of electromyography (EMS) sensors which sense the amplitude, frequency and ischemic changes of various muscle or muscle groups, wherein said sensors, are connected to the seventh signal which is applied to said CPMS control circuit,
e) a range-of-motion (ROM) arm having means for measuring a patient's lateral movement, flexion, extension and rotation, each with six-degrees of freedom, wherein said ROM arm is connected to the eighth signal which is applied to said CPMS control circuit,
f) a set of functional capacity evaluation (FCE) sensors having means for measuring a person's lift, pull and push capability, wherein said circuit is connected to the ninth signal which is applied to said CPMS control circuit,
g) a grip/pinch sensor having means for measuring a patient's hand-grip strength and a pinch strength, wherein said circuit is connected to the tenth signal which is applied to the CPMS control circuit,
h) a power supply interface circuit having an input connected to an external utility power source, said circuit having means for receiving and processing 120–150 volts at 50 or 60 Hz, and means for producing a twenty-first analog power signal and a twenty-third digital power signal, said circuit also having circuit protection in the form of a circuit breaker or a fuse,
i) an analog power supply that when applied the twenty-first signal produces a twenty-second output signal consisting of a regulated 5-volt d-c which powers the analog circuits in said CPMS control circuit,
j) a digital power supply that is isolated from said analog power supply and that when applied the twenty-third output signal produces a twenty-fourth output signal consisting of a regulated 5-volt d-c which powers the digital circuits in said CPMS control circuit,
k) a computer connected to a twenty-fifth signal,
l) a Patient Data Acquisition System (PDAS) software program which resides in said computer, wherein said software provides control and data collection for said CPMS, and,
m) a computer/system interface circuit connected to said computer via the twenty-fifth signal, and to said CPMS control circuit via a twenty-sixth signal, wherein said circuit allows said computer to communicate with said CPMS system.

3. The system as specified in claim 2 wherein said EMG leads connection circuit can accommodate from one to nineteen leads.

4. The system as specified in claim 2 wherein said means in said leads-off detection circuit for determing if the leads are properly attached is by measuring the impedance of the muscles and the surrounding skin area.

5. The system as specified in claim 2 wherein said means in said leads-off display circuit for determining if said electrodes are on or off is by measuring the impedance of each electrode, wherein if the impedance is not at the correct level a corresponding LED illuminates and a signal is sent to said computer which then disables said CPMS.

6. The system as specified in claim 5 wherein a total of 32 electrodes can be utilized.

7. The system as specified in claim 2 wherein the muscle groups monitored by said system comprise:
  a) cervical,
  b) thoraic,
  c) upper extremity,
  d) lower extremity,
  e) lumbosacral, and
  f) chest, wherein data for each muscle group is collected while the muscle group is:
    (1) at rest,
    (2) going through a range of motions,
    (3) at rest,
    (4) being applied a gripping, lifting and pulling force, and
    (5) at rest.

8. The system as specified in claim 7 wherein the cervical muscle group comprises:
  a) fontalis,
  b) massater,
  c) sternocleidomastoid
  d) scalene, and
  e) para cervical.

9. The system as specified in claim 7 Wherein the thoraic muscle group comprises:
  a) trapezii,
  b) seratus
  c) Terres,
  d) latisimis dorsi, and
  e) paraspinal muscles T1–T12.

10. The system as specified in claim 7 wherein the upper extremity muscle group comprises:
  a) deltoid,
  b) bicep
  c) tricep,
  d) flexors/extensors of wrist, and
  e) thenar.

11. The system as specified in claim 7 wherein the lower extremity muscle group comprises:
  a) quads,
  b) hamstrings,
  c) soleus
  d) gastroc,
  e) tibiliar anterior/posterior, and
  f) ankle.

12. The system as specified in claim 7 wherein the lumbosacral muscle group comprises:

a) paraspinal muscles L1–S1,
b) quadratus lumborum,
c) gluteal,
d) abdominal, and
e) obliques.

13. The system as specified in claim 7 wherein the chest muscle group comprises:
a) pectoralis
b) rectus addomidus, and
c) obliques.

14. The system as specified in claim 2 wherein said means in said ROM arm for measuring the lateral movement, flexion, extension and rotation comprises a set of accelerometers or potentiometers.

15. The system as specified in claim 2 wherein said means in said FCE sensors for measuring the lift, pull and push comprises a corresponding set of load cells.

16. The system as specified in claim 2 wherein said means for measuring the hand-grip strength in said grip/pinch sensor comprises a load sensor.

17. The system as specified in claim 16 wherein said means for measuring the pinch strength in said grip/pinch sensor comprises a load button-load cell.

18. The system as specified in claim 2 wherein said data processing circuit comprises a universal serial bus (USB).

19. The system as specified in claim 2 wherein said data processing circuit comprises a Firewire (IEEE 1394) or a parallel port.

20. The system as specified in claim 2 wherein said CPMS can be configured to function as an electrocardiagram (EKG) by monitoring the standard EKG placements via the EMG cable using the EMG sensors plus at least 2 channels of the EMG, sensors to look at vasocontriction which correlates to blood flow.

21. The system as specified in claim 2 wherein said CPMS further comprises a means for allowing the following additional physiological functions to be added:
a) temperature
b) heart rate, and
c) skin response,
d) nerve conduction velocity, and
e) blood flow.

22. The system as specified in claim 2 wherein CPMS comprises:
a) up to 32 channels of surface electromyography (EMG)
b) two functional capacity evaluation (FCE) sensors,
c) two channels of nerve conductive velocity (NCV), with temperature control and pre-set electrodes,
d) two channels of range-of-motion,
e) a grip and pinch strength sensor, and
f) up to 10 channels of EKG.

23. The system as specified in claim 22 wherein said CPMS is designed to conduct an electrodiagnostic functional assessment (EFA) integrated with:
a) electromyogrpah (EMG),
b) functional capacity evaluation (FCE),
c) range of motion,
d) grip and pinch strength, and
e) EKG.

24. The system as specified in claim 22 wherein each channel further comprises an analog-to-digital converter (ADC).

25. The system as specified in claim 2 wherein the signal consists of a cable assembly comprising:

a) two active electrodes,
b) a separation bar which can be locked at a distance between 3 to 5 inches to allow the two active electrodes to remain isolated from each other,
c) a temperature sensor, and
d) a ground connection.

26. The system as specified in claim 2 wherein said computer is comprised of a dedicated PC or laptop computer which operates at least 400 MHz and has at least 64 megabytes of RAM.

27. The system as specified in claim 2 wherein said PDAS software program which resides in said computer is comprised of the following major modules:
a) PDAS start,
b) location,
c) password,
d) reselected patient,
e) patient information
f) select protocol,
g) acquire,
h) scanEMG, and
i) test plot.

28. The system as specified in claim 2 wherein computer interface circuit provides communication control between said CPMS control circuit and said computer.

29. A process utilizing a combined physiological monitoring system (CPMS), to conduct an electrodiagnostic functional assessment (EFA) by analyzing a person's muscle activity by attaching a set of electrodes from said CPMS to selected muscle groups and measuring their electrical activity, wherein the muscle groups and the measurement process comprises:
a) measure the cervical muscle group by, placing a range of motion (ROM) arm on the top of a person's head, take measurements while the person is:
(1) at rest,
(2) performing selected range of motion protocols, and
(3) at rest,
b) measure the thoracic muscle group by placing said ROM arm at the center of the person's mid back and on the shoulders, take measurements while the person is:
(1) at rest,
(2) performing selected range of motion protocols, and
(3) at rest,
c) measure the lumbosacral muscle group by placing said ROM arm at the center of a person's low back, take measurements while the person is:
(1) at rest,
(2) performing selected range of motion protocols, and
(3) at rest,
d) measure the lower extremities muscle group by placing bilateral sets of electrodes on the front and back of a person's thigh and ankles; place said ROM arm on each leg at the hip and knee joint, take measurements while the person is:
(1) at rest,
(2) performing selected range of motion protocols, and
(3) at rest,
e) measure the foot muscle group by placing said ROM arm on the person's ankle, take measurements while the person is:
(1) at rest,
(2) performing selected range of motion protocols, and
(3) at rest, f) measure the upper extremities muscle group by placing said ROM arm on the person's head, on one shoulder and on one wrist, take measurements while the person is:
   (1) at rest,
   (2) performing selected range of motion protocols, and
   (3) at rest,
   (4) performing a grip test utilizing a grip sensor,
   (5) at rest,
   (6) perform a pinch test utilizing a pinch sensor which is placed between the thumb and forefinger,
   (7) at rest,
g) measure the hand muscle group by placing said ROM arm on the person's wrist, take measurements while the person is:
   (1) at rest,
   (2) performing selected range of motion protocols,
   (3) at rest,
   (4) performing a pinch test utilizing a pinch sensor which is placed between the thumb and the forefinger,
   (5) at rest, and
h) measure the face muscle group by placing said ROM arm on top of TMJ, take measurements while the person is:
   (1) at rest,
   (2) performing selected range of motion protocols, and
   (3) at rest.

30. The system as specified in claim 29 wherein:
   a) the cervical muscle group comprises: sternocleidomastoid, scalene, paracervical, and upper trapzii,
   b) the thoraic muscle group comprises: mid trapezii, lower trapezii, paraspinal muscles T5–T8, T8–T12, terses, and seratus,
   c) the lumbosacral muscle group comprises: paraspinal muscles L1–L3, L5–L51, quaratus lumborum, gluteal muscles, abdominal, and hamstrings,
   d) the lower extremities muscle group comprises:
   e) the foot muscle group comprises: all muscles in pelvis, leg and feet,
   f) the upper extremities muscle group comprises: bilateral SCM, scalene, deltoid, biceps, triceps, and wrist flexors/extensors,
   g) the hand muscle group comprise: all muscles in the hand,
   h) the face muscle group comprise: fontalis, massater TMJ.

* * * * *